United States Patent [19]
Doria et al.

[11] 4,251,531
[45] Feb. 17, 1981

[54] 3,4-DIHYDRO-QUINAZOLINE DERIVATIVES

[75] Inventors: Gianfederico Doria, Milan; Ciriaco Romeo, Serino; Piernicola Giraldi, Milan; Francesco Lauria, Milan; Maria L. Corno, Milan; Piero Sberze, Varese; Marcello Tibolla, Canale d'Agordo, all of Italy

[73] Assignee: Farmitalia Carlo Erba S.p.A., Milan, Italy

[21] Appl. No.: 738,221

[22] Filed: Nov. 2, 1976

[30] Foreign Application Priority Data

Dec. 5, 1975 [IT] Italy ................................ 29998 A/75

[51] Int. Cl.³ ................ C07D 239/82; A61K 31/505
[52] U.S. Cl. ................................ 424/251; 424/248.4; 424/248.5; 544/116; 544/284; 544/289
[58] Field of Search ................ 260/25 QA, 256.4 Q; 544/284, 289, 116; 424/248.5, 248.4, 251

[56] References Cited
U.S. PATENT DOCUMENTS 3,696,102  10/1972  Cronin ........................ 260/251 QA

FOREIGN PATENT DOCUMENTS 2106946  9/1971  Fed. Rep. of Germany .
2134263  2/1972  Fed. Rep. of Germany .
2078650  11/1971 France .
1301319  9/1972  United Kingdom .

OTHER PUBLICATIONS

Inoue, et al.–C.A. 81, 77957x, (1974).
Arcoria, et al.–C.A. 66, 38862h, (1967).
Goose, et al., "Immunology", vol. 16, 1969, pp. 749–760.
Binaghi, et al., "J. Immunology", vol. 92, 1964, pp. 920–926.
Mota, "Immunology", vol. 7, 1964, pp. 611–699.
Finney, "Statistical Methods in Biological Assay", pp. 118–119.

Primary Examiner—Donald G. Daus
Assistant Examiner—James H. Turnipseed
Attorney, Agent, or Firm—Murray and Whisenhunt

[57] ABSTRACT 3,4-Dihydro-quinazoline derivatives, such as 6-carboxy-2-(2'-ethoxy-phenyl)-3,4-dihydro-4-oxo-quinazoline, are disclosed. The compounds possess anti-allergy properties and can be used for the treatment of allergic conditions.

15 Claims, No Drawings

3,4-DIHYDRO-QUINAZOLINE DERIVATIVES

The present invention relates to 3,4-dihydro-quinazoline derivatives, to a process of their preparation and to pharmaceutical compositions containing them.

The compounds of the invention have the following formula (I)

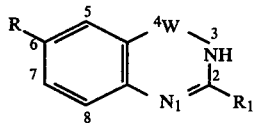
(I)

wherein

R is (a) esterified or unesterified carboxy or the radical

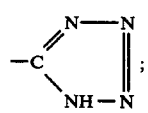

(b) —COR₃ wherein R₃ is —NHOH or

wherein each of R₄ and R₅ is independently hydrogen or $C_1$–$C_{10}$ alkyl or, when R₄ is hydrogen, R₅ may also be (a′) the radical

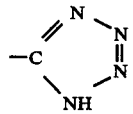

or (b′) the group

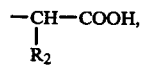

wherein R₂ is hydrogen or $C_1$–$C_6$ alkyl or R₄ and R₅, taken together with the nitrogen atom, form a N-pyrrolidinyl, piperidino or morpholino radical; R₁ is (a″) $C_2$–$C_{20}$ alkyl or $C_2$–$C_{20}$ alkenyl, being the alkyl or alkenyl group unsubstituted or substituted by one or more substituents selected from the group consisting of halogen, hydroxy, $C_1$–$C_6$ alkoxy, acyloxy and

wherein R₄ and R₅ are as defined above, or (b″) the radical

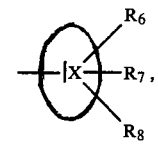

wherein each of R₆, R₇ and R₈, which may be the same or different, is selected from the group consisting of hydrogen; halogen; hydroxy;

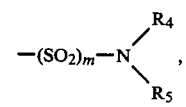

wherein m is zero or 1 and R₄ and R₅ are as defined above; and —(Y)ₘ—R₉ wherein m is as defined above, Y is an oxygen or sulphur atom and R₉ is a $C_1$–$C_{12}$ alkyl or $C_3$–$C_{12}$ alkenyl, being the alkyl or alkenyl group unsubstituted or substituted by one or more substituents selected from the group consisting of halogen, carboxy, $C_2$–$C_6$ carbalkoxy, hydroxy, $C_1$–$C_6$ alkoxy, acyloxy, unsubstituted or substituted phenyl and

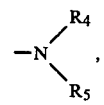

wherein R₄ and R₅ are as defined above; or R₆ and R₇, when placed on adjacent carbon atom, may represent, taken together, a methylenedioxy, ethylenedioxy or propylenedioxy group, and wherein X is phenyl or a pentatomic or hexatomic heteromonocyclic ring containing one or two heteroatoms selected from the group consisting of nitrogen, oxygen and sulphur; W is >C═O or >C═S.

Object of the present invention are also the salts of the compounds of formula (I) either with pharmaceutically acceptable bases or with pharmaceutically acceptable acids.

It is also to be noted that the above definition of the compounds of the invention includes all the possible isomers (e.g. the cis and trans isomers) and steroisomers, as well as their mixtures.

The alkyl, alkenyl, alkoxy, acyloxy and carbalkoxy groups may be branched or straight chain. The numbering used to identify the position of the substituents in the X radical is the conventional one, as is shown by the following examples:

(a) when X is phenyl:

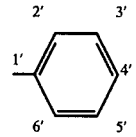

(b) when X is a pentatomic heteromonocyclic radical:

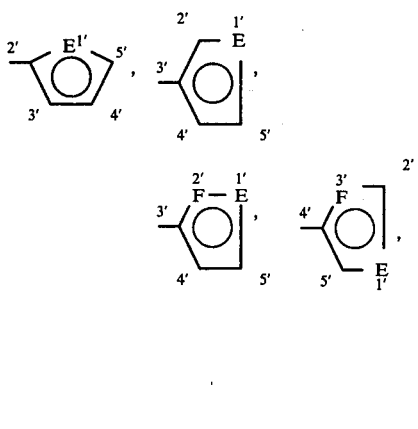

wherein E and F are heteroatoms;
(c) when X is a hexatomic heteromonocyclic radical:

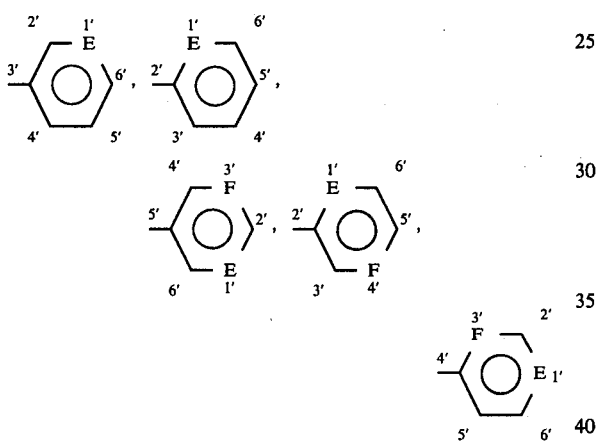

wherein E and F are heteroatoms.

When R is an esterified carboxy group, it is preferably the group —COOR$_9$ wherein R$_9$ is as defined above.

When one of R$_4$ and R$_5$ is C$_1$–C$_{10}$ alkyl, it is preferably C$_1$–C$_4$ alkyl, in particular methyl, ethyl, isopropyl and t-butyl.

When R$_2$ is alkyl, it is preferably methyl or ethyl.

When R$_1$ is alkyl, it is preferably C$_2$–C$_{11}$ alkyl, in particular ethyl, propyl, isopropyl, butyl, 2'-methyl-propyl, pentyl, 2',2'-dimethylpropyl, hexyl, heptyl, 2'-ethyl-pentyl, nonyl, undecyl or tridecyl, pentadecyl or heptadecyl, being the C$_2$–C$_{11}$ alkyl unsubstituted or substituted by one or more, preferably one, substituents selected from the group consisting of bromine, chlorine, hydroxy, methoxy, ethoxy, acetoxy, amino, dimethylamino or diethylamino.

When R$_1$ is alkenyl, it is preferably 1'-trans-propenyl or 8'-cis-heptadecenyl.

A C$_2$–C$_6$ carbalkoxy group is preferably carbomethoxy or carbethoxy; a C$_1$–C$_6$ alkoxy group is preferably methoxy or ethoxy; an acyloxy group is preferably a C$_2$–C$_{18}$ aliphatic acyloxy group, which may be branched or straight chain, in particular acetoxy, propionyloxy, stearoyloxy, pivaloyloxy and oleoyloxy.

R$_9$ is preferably a C$_1$–C$_{12}$ alkyl group, in particular methyl, ethyl, propyl, isopropyl, butyl, t-butyl, octyl or undecyl, which may be optionally substituted as defined above, preferably by methoxy, ethoxy, dimethylamino, diethylamino. When R$_9$ is a C$_3$–C$_{12}$ alkenyl group, it is preferably allyl or 2-butenyl.

When these alkyl or alkenyl groups are substituted by a phenyl group, the phenyl group may be in turn substituted by one or more substituents, preferably selected from the group consisting of acetyl, hydroxy, C$_1$–C$_6$ alkyl, preferably methyl, C$_1$–C$_6$ alkoxy, preferably methoxy, and halogen, preferably chlorine.

When X is a heteromonocyclic ring, it is preferably furyl, thienyl, pyridyl or pyrazinyl.

Particularly preferred compounds are those of formula (I) wherein R is salified or unsalified carboxy or the radical

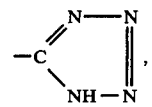

W is >C=O,
R$_1$ is (1) phenyl, which may be optionally substituted by one or more substituents selected from the group consisting of (a''')—(O)$_m$—R$_9$, wherein m is as defined above and R$_9$ is C$_1$–C$_6$ alkyl, preferably methyl, ethyl, propyl, isopropyl, butyl and sec.butyl, which may be unsubstituted or substituted by a hydroxy group or by a C$_1$–C$_4$ alkoxy group, in particular methoxy and ethoxy; (b''') a halogen atom, in particular fluorine and chlorine; (c''') and a group

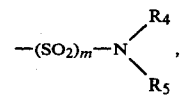

wherein m is as defined above and each of R$_4$ and R$_5$, which may be the same or different, is hydrogen or C$_1$–C$_4$ alkyl, preferably ethyl, methyl, isopropyl, sec.butyl and t-butyl, or (2) pyridyl, which may be unsubstituted or substituted by a C$_1$–C$_4$ alkoxy group, preferably methoxy, ethoxy, isopropoxy and n-butoxy, or (3) a C$_4$–C$_9$ alkyl, in particular butyl, 2'-methyl-propyl, pentyl, 2',2'-dimethylpropyl, hexyl, heptyl, 2'-ethyl-pentyl, nonyl.

When R$_1$ is mono-substituted phenyl, the substituent is preferably in the 2'-position.

When R$_1$ is a phenyl substituted by two or more substituents, at least a substituent is preferably in the 2'-position.

When R$_1$ is a 2'-pyridyl substituted by a C$_1$–C$_4$ alkoxy group, the alkoxy group is preferably in the 3'-position.

Examples of pharmaceutically acceptable salts with bases are either those with inorganic bases, such as sodium, potassium, calcium and aluminium hydroxides, or with organic bases, such as lysine, triethylamine, procaine, dibenzylamine, N-benzyl-β-phenethylamine, N,N'-dibenzylethylenediamine, dehydroabiethylamine, N-ethylpiperidine and the other organic amines, as well as the salts with inorganic, e.g. hydrochloric, hydrobromic and sulphuric, acids and with organic acids e.g. citric, tartaric, maleic, fumaric and methanesulphonic acid. Preferred salts are the sodium and potassium salts as well as the hydrochlorides of the basic esters, e.g. the diethylaminoethanol, morpholinoethanol and N-pyrrolidinylethanol ester.

Example of particularly preferred compounds of the invention are:

6-carboxy-2-(2'-methoxy-phenyl)-3,4-dihydro-4-oxo-quinazoline;
6-carboxy-2-(2'-ethoxy-phenyl)-3,4-dihydro-4-oxo-quinazoline;
6-carboxy-2-(2'-allyloxy-phenyl)-3,4-dihydro-4-oxo-quinazoline;
6-carboxy-2-(2'-propoxy-phenyl)-3,4-dihydro-4-oxo-quinazoline;
6-carboxy-2-(2'-butoxy-phenyl)-3,4-dihydro-4-oxo-quinazoline;
6-carboxy-2(2'-isopropoxy-phenyl)-3,4-dihydro-4-oxo-quinazoline;
6-carboxy-2-[2'-(1-methyl-propoxy)-phenyl]-3,4-dihydro-4-oxo-quinazoline;
6-carboxy-2-[2'-(2-methyl-propoxy)-phenyl]-3,4-dihydro-4-oxo-quinazoline;
6-carboxy-2-[2'-(2-ethoxy-ethoxy)-phenyl]-3,4-dihydro-4-oxo-quinazoline;
6-carboxy-2-[4'-(2-ethoxy-ethoxy)-phenyl]-3,4-dihydro-4-oxo-quinazoline;
6-carboxy-2-(2'-fluoro-phenyl)-3,4-dihydro-4-oxo-quinazoline;
6-carboxy-2-(3'-fluoro-phenyl)-3,4-dihydro-4-oxo-quinazoline;
6-carboxy-2-(4'-fluoro-phenyl)-3,4-dihydro-4-oxo-quinazoline;
6-carboxy-2-(2'-chloro-phenyl)-3,4-dihydro-4-oxo-quinazoline;
6-carboxy-2-(2'-methyl-phenyl)-3,4-dihydro-4-oxo-quinazoline;
6-carboxy-2-(3'-methyl-phenyl)-3,4-dihydro-4-oxo-quinazoline;
6-carboxy-2-(4'-methyl-phenyl)-3,4-dihydro-4-oxo-quinazoline;
6-carboxy-2-(4'-isopropyl-phenyl)-3,4-dihydro-4-oxoquinazoline;
6-carboxy-2-(3',4'-dimethoxy-phenyl)-3,4-dihydro-4-oxo-quinazoline;
6-carboxy-2-(2'-amino-phenyl)-3,4-dihydro-4-oxo-quinazoline;
6-carboxy-2-(2'-methoxy-5'-methyl-phenyl)-3,4-dihydro-4-oxo-quinazoline;
6-carboxy-2-(2'-methoxy-4'-methyl-phenyl)-3,4-dihydro-4-oxo-quinazoline;
6-carboxy-2-(2'-isopropoxy-5'-methyl-phenyl)-3,4-dihydro-4-oxo-quinazoline;
6-carboxy-2-(2'-isopropoxy-4'-methyl-phenyl)-3,4-dihydro-4-oxo-quinazoline;
6-carboxy-2-(2'-butoxy-5'-methyl-phenyl)-3,4-dihydro-4-oxo-quinazoline;
6-carboxy-2-(2'-butoxy-4'-methyl-phenyl)-3,4-dihydro-4-oxo-quinazoline;
6-carboxy-2-(2',5'-dimethoxy-phenyl)-3,4-dihydro-4-oxo-quinazoline;
6-carboxy-2-(2',6'-dimethoxy-phenyl)-3,4-dihydro-4-oxo-quinazoline;
6-carboxy-2-(2',4'-dimethoxy-phenyl)-3,4-dihydro-4-oxo-quinazoline;
6-carboxy-2-(2'-methoxy-5'-fluoro-phenyl)-3,4-dihydro4-oxo-quinazoline;
6-carboxy-2-(2'-methoxy-5'-aminosulfonyl-phenyl)-3,4-dihydro-4-oxo-quinazoline;
6-carboxy-2-(2'-isopropoxy-5'-aminosulfonyl-phenyl)-3,4-dihydro-4-oxo-quinazoline;
6-carboxy-2-(2'-butoxy-5'-aminosulfonyl-phenyl)-3,4-dihydro-4-oxo-quinazoline;
6-carboxy-2-(2'-methoxy-5'-N-ethylaminosulfonyl-phenyl)-3,4-dihydro-4-oxo-quinazoline;
6-carboxy-2-(2'-isopropoxy-5'-N-ethylaminosulfonyl-phenyl)-3,4-dihydro-4-oxo-quinazoline;
6-carboxy-2-(2'-butoxy-5'-N-ethylaminosulfonyl-phenyl)-3,4-dihydro-4-oxo-quinazoline;
6-carboxy-2-(2'-methoxy-5'-N-isopropylaminosulfonyl-phenyl)-3,4-dihydro-4-oxo-quinazoline;
6-carboxy-2-(2'-isopropoxy-5'-N-isopropylaminosulfonyl-phenyl)-3,4-dihydro-4-oxo-quinazoline;
6-carboxy-2-(2'-butoxy-5'-N-isopropylaminosulfonyl-phenyl)-3,4-dihydro-4-oxo-quinazoline;
6-carboxy-2-(2'-methoxy-5'-N-tertbutylaminosulfonyl-phenyl)-3,4-dihydro-4-oxo-quinazoline;
6-carboxy-2-(2'-isopropoxy-5'-N-tertbutylaminosulfonyl-phenyl)-3,4-dihydro-4-oxo-quinazoline;
6-carboxy-2-(2'-butoxy-5'-N-tertbutylaminosulfonyl-phenyl)-3,4-dihydro-4-oxo-quinazoline;
6-carboxy-2-(2'-methoxy-5'-N-methyl-N-ethyl-aminosulfonyl-phenyl)-3,4-dihydro-4-oxo-quinazoline;
6-carboxy-2-(2'-methoxy-5'-N-methyl-N-isopropylaminosulfonyl-phenyl)-3,4-dihydro-4-oxo-quinazoline;
6-carboxy-2-(2'-methoxy-5'-N-methyl-N-tertbutylaminosulfonyl-phenyl)-3,4-dihydro-4-oxo-quinazoline;
6-carboxy-2-(2'-methoxy-5'-N,N-diethylaminosulfonyl-phenyl)-3,4-dihydro-4-oxo-quinazoline;
6-carboxy-2-(2'-pyridyl)-3,4-dihydro-4-oxo-quinazoline;
6-carboxy-2-(2'-pyrazinyl)-3,4-dihydro-4-oxo-quinazoline;
6-carboxy-2-(3'-methoxy-2'-pyridyl)-3,4-dihydro-4-oxo-quinazoline;
6-carboxy-2-(3'-isopropoxy-2'-pyridyl)-3,4-dihydro-4-oxo-quinazoline;
6-carboxy-2-(3'-butoxy-2'-pyridyl)-3,4-dihydro-4-oxo-quinazoline;
6-carboxy-2-(3'-ethoxy-2'-pyridyl)-3,4-dihydro-4-oxo-quinazoline;
6-carboxy-2-(3'-propoxy-2'-pyridyl)-3,4-dihydro-4-oxo-quinazoline;
6-(5-tetrazolyl)-2-(2'-ethoxy-phenyl)-3,4-dihydro-4-oxo-quinazoline;
6-(5-tetrazolyl)-2-(2'-methoxy-phenyl)-3,4-dihydro-4-oxo-quinazoline;
6-(5-tetrazolyl)-2-(2'-butoxy-phenyl)-3,4-dihydro-4-oxo-quinazoline;
6-(5-tetrazolyl)-2-(2'-isopropoxy-phenyl)-3,4-dihydro-4-oxo-quinazoline;
6-(5-tetrazolyl)-2-(2'-methoxy-4'-methyl-phenyl)-3,4-dihydro-4-oxo-quinazoline;
6-(5-tetrazolyl)-2-(2'-methoxy-5'-methyl-phenyl)-3,4-dihydro-4-oxo-quinazoline;
6-(5-tetrazolyl)-2-(2',6'-dimethoxy-phenyl)-3,4-dihydro-4-oxo-quinazoline;
6-carboxy-2-pentyl-3,4-dihydro-4-oxo-quinazoline;
6-carboxy-2-propyl-3,4-dihydro-4-oxo-quinazoline;
6-carboxy-2-isopropyl-3,4-dihydro-4-oxo-quinazoline;
6-carboxy-2-butyl-3,4-dihydro-4-oxo-quinazoline;
6-carboxy-2-(2'-methyl-propyl)-3,4-dihydro-4-oxo-quinazoline;

6-carboxy-2-(2',2'-dimethyl-propyl)-3,4-dihydro-4-oxo-quinazoline;
6-carboxy-2-hexyl-3,4-dihydro-4-oxo-quinazoline;
6-carboxy-2-heptyl-3,4-dihydro-4-oxo-quinazoline;
6-carboxy-2-nonyl-3,4-dihydro-4-oxo-quinazoline;
6-carboxy-2-undecyl-3,4-dihydro-4-oxo-quinazoline;
6-carboxy-2-(1'-trans-propenyl)-3,4-dihydro-4-oxo-quinazoline;
6-carboxy-2-(8'-cis-heptadecenyl)-3,4-dihydro-4-oxo-quinazoline;
6-carboxy-2-(2'-ethyl-pentyl)-3,4-dihydro-4-oxo-quinazoline;
6-carboxy-2-(2'-methoxy-propyl)-3,4-dihydro-4-oxo-quinazoline;
6-carboxy-2-(2'-hydroxy-propyl)-3,4-dihydro-4-oxo-quinazoline;
6-carboxy-2-(2'-isopropoxy-phenyl)-3,4-dihydro-4-thio-quinazoline;
6-carboxy-2-(2'-butoxy-phenyl)-3,4-dihydro-4-thio-quinazoline;
6-carboxy-2-(2'-methoxy-phenyl)-3,4-dihydro-4-thio-quinazoline;

as well as the pharmaceutically acceptable salts thereof, in particular, the sodium salts and the hydrochlorides of the basic esters (in particular of those with diethylamino-ethanol, dimethylamino-ethanol, morpholino-ethanol and N-pirrolidinyl-ethanol), the amides (in particular N,N-diethylamide and N-tetrazolyl-amide) and the esters, in particular the ethyl, isopropyl, t-butyl, octyl and pivaloyloxymethyl ester.

The compounds of the invention are prepared by a processing comprising:

(a) cyclizing a compound of formula (II)

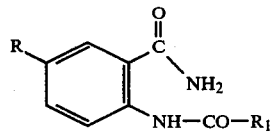

(II)

wherein
R and $R_1$ are as defined above, so obtaining compounds of formula (I) wherein W is $>C=O$; or
(b) oxidizing a compound of formula (III)

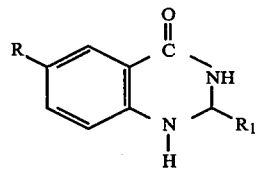

(III)

wherein
R and $R_1$ are as defined above, so obtaining compounds of formula (I) wherein W is $>C=O$; or
(c) cyclizing a compound of formula (IV)

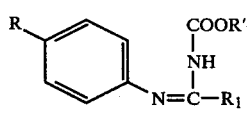

(IV)

wherein
R' is an alkyl group and

R and $R_1$ are as defined above, so obtaining compounds of formula (I), wherein W is $>C=O$;
and, is desired, converting a compound of formula (I) wherein W is $>C=O$ into a compound of formula (I) wherein W is $>C=S$ and/or, if desired, converting a compound of formula (I) into another compound of formula (I) by known methods and/or, if desired, converting a compound of formula (I) into a pharmaceutically acceptable salt and/or, if desired, converting a salt into a free compound and/or, if desired, resolving a mixture of isomers into the single isomers.

The cyclization of the compound of formula (II) may be carried out, e.g., at a temperature ranging from the room temperature to about 300° C., either in the absence of solvents or in the presence of solvents such as, for example, lower aliphatic alcohols, in particular methanol and ethanol, diluted ammonium, sodium and potassium hydroxide, benzene, toluene, xylene, pyridine, tetrahydrofuran, dioxane, dimethylformamide, ethyl orthoformate, formic acid, acetic acid and their mixtures, using as dehydrating agent, if necessary, acetic anhydride, $PCl_3$, $POCl_3$, polyphosphoric acid or dicyclohexylcarbodiimide.

The oxidation of the compound of formula (III) may be carried out, for example, with potassium permanganate in acetone or with chromium trioxide in acetic acid at a temperature ranging from about 0° C. to about 30° C.

The cyclization of the compound of formula (IV) may be carried out, for example, in an inert solvent such as toluene and xylene at temperatures ranging from about 50° C. to about 150° C. in the presence of an acid condensing agent, such as, for example, $P_2O_5$ or $H_3PO_4$.

In the compound of formula (IV) R' is preferably a lower alkyl group, e.g., a $C_1$–$C_6$ alkyl group, preferably methyl or ethyl.

A compound of formula (I) wherein W is $>C=O$ may be converted into a compound of formula (I) wherein W is $>C=S$ by reaction, e.g., with $P_2S_5$ in an inert solvent such as benzene, toluene, xylene, pyridine, at a temperature ranging from the room temperature to about 150° C. As stated above, a compound of formula (I) may be converted into another compound of formula (I) by known methods.

For example, a compound of formula (I), wherein R is an esterified carboxy group, may be converted into a compound of formula (I), wherein R is carboxy, by basic hydrolysis, using, e.g., sodium potassium hydroxide, in a solvent such as water or a lower aliphatic alcohol, and operating at a temperature ranging from the room temperature to about 150° C.; the same reaction may be carried out by treatment with lithium bromide in dimethylformamide at a temperature higher than 50° C.

A compound of formula (I) wherein R is carboxy, may be converted into a compound of formula (I) wherein R is an esterified carboxy group, e.g., a carbalkoxy group, by esterification, for example, by reaction of the alkaline salt of the acid with the suitable alkyl halide, in an inert solvent such as acetone, dioxane, dimethylformamide, hexamethylphosphorotriamide at a temperature ranging from about 0° C. to about 100° C.

Free hydroxy groups may be etherified, for example, by treatment with alkyl halides and a basis, such as sodium hydride or potassium carbonate, in a solvent such as acetone, dioxane and dimethylformamide, at a temperature varying between about 0° C. and about 100° C.; etherified hydroxy groups may be converted into free hydroxy groups, for example, by treatment with pyridine chloride or hydrobromic, hydrochloric and hydroiodic acid in a solvent such as acetic acid, at a temperature ranging from about 30° C. to the reflux temperature.

A compound of formula (I), wherein R is carboxy, may be converted into a compound of formula (I), wherein R is the radical

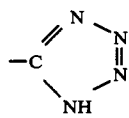

by known methods, for example, by converting the carboxy group into the corresponding halide, preferably the chloride, by reaction, e.g., with thionyl chloride in benzene or dioxan or dichloroethane, at a temperature ranging from the room temperature to about 100° C., then by reacting the halide with ammonia, at room temperature in one of the above mentioned solvents, to give the corresponding amide and by dehydrating the amide to give the nitrile, e.g., by means of p-toluenesulphonyl chloride in pyridine and dimethylformamide, at a temperature ranging from about 30° C. to about 100° C., and finally reacting the nitrile with sodium azide and ammonium chloride in dimethylformamide at a temperature ranging from the room temperature to about 100° C.

Also the optional salification of a compound of formula (I) as well as the conversion of a salt into the free compound and the resolution of a mixture of isomers into the single isomers may be effected by conventional methods. The compounds of formula (II) may be prepared, for example:

(a') by reaction of a compound of formula (V)

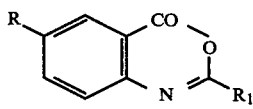 (V)

wherein R and $R_1$ are as defined above, with ammonium hydroxide; this reaction is preferably performed at a temperature ranging from the room temperature to 200° C., either in the absence of solvents or in an inert organic solvent such as lower aliphatic alcohols, dioxane and dimethylformamide; (b') by reaction of a compound of formula (VI)

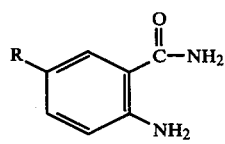 (VI)

wherein R is as defined above, with the anhydride or the chloride of an acid of formula $R_1$—COOH, wherein $R_1$ is as defined above; this reaction is preferably performed at a temperature ranging from the room temperature to 150° C., either in the presence of a solvent such as, e.g., benzene, toluene, xylene, pyridine, dioxane, dimethyl formamide or in the absence of solvents, using a basis such as, for example, sodium bicarbonate, sodium carbonate, pyridine, triethylamine, as acid acceptor.

The compounds of formula (III) may be prepared, for example, by reaction of the compound of formula (VI) with an aldehyde of formula $R_1$—CHO, wherein $R_1$ is as defined above, in an inert solvent such as benzene, toluene, xylene, dioxane, ethanol, dimethoxyethane, bis(2-methoxyethyl) ether and dimethylformamide, and in the presence of a basic or acid catalyst such as piperidine, hydrochloric acid, sulphuric acid, p-toluenesulphonic acid, at a temperature ranging from the room temperature to 150° C.

The compounds of formula (IV) may be prepared, for example, by reacting a compound of formula (VII)

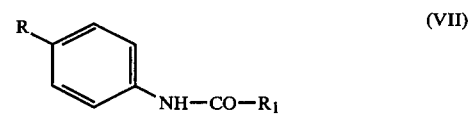 (VII)

wherein

R and $R_1$ are as defined above, with an alkyl carbamate, preferably a lower alkyl carbamate, for example, methyl carbamate or ethyl carbamate, in an inert solvent such as toluene and xylene at temperatures ranging from about 0° C. to about 150° C., preferably in the presence of a dehydrating agent such as, for example, $P_2O_5$.

The compounds of formula (V) may be in turn prepared, e.g., by heating a compound of formula (VIII)

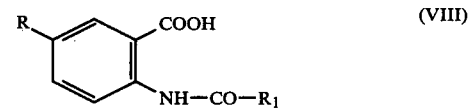 (VIII)

wherein R and $R_1$ are as defined above, in acetic anhydride at a temperature ranging from 50° C. to the reflux temperature.

The compounds of formula (VIII) may be prepared, for example, by reaction of a compound of formula (IX)

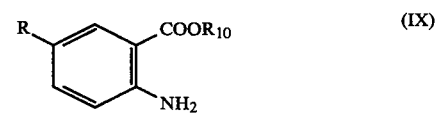 (IX)

wherein R is as defined above and $R_{10}$ is hydrogen or alkyl, in particular $C_1$–$C_4$ alkyl, with the anhydride or the chloride of an acid of formula $R_1$—COOH, wherein $R_1$ is as defined above, at a temperature ranging from the room temperature to 150° C., either in the presence of solvents, such as benzene, toluene, dioxane, pyridine or in the absence of solvents, using a basis, such as sodium bicarbonate, sodium carbonate, pyridine, triethylamine, as acid acceptor and by subsequent basic hydrolysis of the ester group, i.e., when $R_{10}$ is alkyl, with sodium or potassium hydroxide in a solvent such as water, lower aliphatic alcohols, in particular ethanol, dioxane and their mixtures at a temperature ranging from 10° C. to 100° C. The compounds of formula (VI) may be prepared by known methods, e.g., by reduction of the corresponding nitro-derivatives or by reaction of a compound of formula (X)

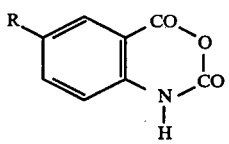

wherein R is as defined above, with ammonium hydroxide, either in the absence of solvents or in the presence of organic solvents, such as methanol, ethanol, dioxane, dimethylformamide, pyridine at a temperature ranging from −30° C. to 200° C. The compounds of formula (X) may be in turn prepared from a compound of formula (IX) wherein $R_{10}$ is hydrogen, by one of the following methods:

(a'') by reaction with phosgene at room temperature in an acidic aqueous medium;

(b'') by reaction with ethyl chloroformate, at a temperature ranging from 50° C. to 120° C., either in the absence or in the presence of solvents such as dioxane, benzene, toluene, xylene to obtain the corresponding N-carbethoxy derivative and by subsequent cyclization, which may be carried out by using an excess of ethyl chloroformate or with acetyl chloride or with $PBr_3$, at a temperature ranging from 50° C. to 150° C.

The compounds of formula (IX) are known compounds and may be prepared by known methods, for example, by reduction, in a conventional manner, of the corresponding nitro-derivatives.

Also the compounds of formula (VII) are known compounds. The compounds of the invention possess anti-allergic activity, as is shown by the fact that they are active in the passive cutaneous anaphylaxis (PCA) test in rats, according to Goose Y. and Blair A.M.Y.N. (Immunology, 1969, 16:749).

They can be therefore used in prevention and treatment of bronchial asthma, allergic rhinitis, hay fever, urticaria and dermatosis. An important peculiarity of the compounds is that they exhibit anti-allergic activity also when orally administered.

The compounds of the invention may be administered in conventional manner, for instance, orally and parenterally at a daily dosage preferably of 0.5 to 15 mg/kg, or by inhalation, preferably at a daily dosage of 0.5 to 100 mg; preferably 0.5 to 25 mg, or by topical application.

The nature of the pharmaceutical compositions containing the compounds of this invention in association with pharmaceutically acceptable carriers or diluents will, of course, depend upon the desired mode of administration.

The compositions may be formulated in the conventional manner with the usual ingredients. For example, the compounds of the invention may be administered in the form of aqueous or oily solutions or suspensions, aerosols, as well as powders, tablets, pills, gelatine capsules, syrups, or creams, or lotions for topical use.

Thus, for oral administration, the pharmaceutical compositions containing the compounds of this invention, are preferably tablets, pills or gelatine capsules which contain the active substance together with diluents, such as, for example, lactose, dextrose, sucrose, mannitol, sorbitol, cellulose; lubricants, for instance, silica, talc, stearic acid, magnesium or calcium stearate, and/or polyethylene glycols; or they may also contain binders, such as, for example, starches, gelatine, methylcellulose, carboxymethylcellulose, gum-arabic, tragacanth, polyvinylpyrrolidone, disintegrating agents, such as, for instance, starches, alginic acid, alginates, sodium starch glycolate; effervescing mixtures; dyestuffs; sweeteners; wetting agents, such as, for instance, lecithin, polisorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

For the treatment of allergic asthma, the compounds of the invention are also administered by inhalation. For such use, suitable compositions may comprise a suspension or solution of the active ingredient, preferably in the form of a salt, such as the sodium salt, in water, for administration by means of a conventional nebulizer. Alternatively, the compositions may comprise a suspension or a solution of the active ingredient in a conventional liquified propellant, such as, dichlorodifluoromethane or dichlorotetrafluoroethane to be administered from a pressurized container, i.e., an aerosol dispenser. When the medicament is not soluble in the propellant, it may be necessary to add a co-solvent, such as, ethanol, dipropylene glycol, isopropyl myristate, and/or a surface-active agent to the composition, in order to suspend the medicament in the propellant medium and such surface-active agents may be any of those commonly used for this purpose, such as non-ionic surface-active agents, e.g., lecithin. The compounds of the invention may also be administered in the form of powders by means of a suitable insufflator device and in this case the fine particle sized powders of the active ingredient may be mixed with a diluent material such as lactose.

Furthermore, the compounds of this invention may also be administered by intradermal or intravenous injection in the conventional manner.

In addition to the internal administration, the compounds of this invention may find use in compositions for topical application, e.g. as creams, lotions or pastes for use in dermatological treatments. For these compositions the active ingredient may be mixed with conventional oleaginous or emulsifying excipients.

The following examples illustrate but do not limit the present invention.

EXAMPLE 1

Dimethyl-4-amino-isophthalate (10 g) in 10 ml of dioxane and 20 ml of anhydrous pyridine are treated with 20 g of 2-isopropoxy-benzoyl chloride at room temperature, overnight. After dilution with water, the precipitate is collected, dissolved in ethyl acetate, and washed with 5% $NaHCO_3$ and then with water. After evaporation to dryness under vacuum, the material is crystallized from isopropyl ether, yielding dimethyl-4-(2'-isopropoxybenzoylamino)-isophthalate (12.3 g; m.p. 107°–110° C.), which is dissolved in 80 ml of dioxane and treated with 80 ml of 1 N NaOH at room temperature for one night. After acidification with dilute HCl, the precipitate is collected under vacuum and washed with water until neutral. The yield is 10.9 g of 4-(2'-isopropoxybenzoylamino)-isophthalic acid, which are treated with 60 ml of acetic anhydride at 90°–100° C. for 15'. After cooling, dilute with 60 ml of isopropyl ether and filter. The yield is 9 g of 6-carboxy-2-(2'-isopropoxyphenyl)-4H-3,1-benzoxazin-4-one (m.p. 246°–250° C.), which are reacted at room temperature first with 90 ml of 32% ammonium hydroxide and then with 45 ml of 2 N NaOH for 120'. After acidification with 4 N HCl, the precipitate is filtered off and crystallized from ethanol-chloroform to give 6-carboxy-2-(2'-isopropoxyphenyl)-3,4-dihydro-4-oxo-quinazoline (6.6 g; m.p. 316°–318° C.).

Analogously, the following compounds were obtained:

6-carboxy-2-(2'-methoxy-phenyl)-3,4-dihydro-4-oxo-quinazoline, m.p. 295°–7° C.;
6-carboxy-2-(2'-ethoxy-phenyl)-3,4-dihydro-4-oxo-quinazoline; m.p. 305°–308° C.;
6-carboxy-2-(2'-allyloxy-phenyl)-3,4-dihydro-4-oxo-quinazoline, m.p. >300° C. (dec.);
6-carboxy-2-[4'-(2-ethoxy-ethoxy)-phenyl]-3,4-dihydro-4-oxo-quinazoline, m.p. 303°–306° C.;
6-carboxy-2-(2'-propoxy-phenyl)-3,4-dihydro-4-oxo-quinazoline, m.p. 285°–286° C.;
6-carboxy-2-(2'-butoxy-phenyl)-3,4-dihydro-4-oxo-quinazoline, m.p. 258°–260° C.;
6-carboxy-2-[2'-(1-methyl-propoxy)-phenyl]-3,4-dihydro-4-oxo-quinazoline;
6-carboxy-2-[2'-(2-methyl-propoxy)-phenyl]-3,4-dihydro-4-oxo-quinajzoline, m.p. 299°–301° C.;
6-carboxy-2-[2'-(2-ethoxy-ethoxy)-phenyl]-3,4-dihydro-4-oxo-quinazoline, m.p. 242°–244° C.;
6-carboxy-2-(2'-methoxy-5'-methyl-phenyl)-3,4-dihydro-4-oxo-quinazoline;
6-carboxy-2-(2'-methoxy-4'-methyl-phenyl)-3,4-dihydro-4-oxo-quinazoline;
6-carboxy-2-(2'-isopropoxy-5'-methyl-phenyl)-3,4-dihydro-4-oxo-quinazoline;
6-carboxy-2-(2'-isopropoxy-4'-methyl-phenyl)-3,4-dihydro-4-oxo-quinazoline;
6-carboxy-2-(2'-butoxy-5'-methyl-phenyl)-3,4-dihydro-4-oxo-quinazoline;
6-carboxy-2-(2'-butoxy-4'-methyl-phenyl)-3,4-dihydro-4-oxo-quinazoline;
6-carboxy-2-(2',4'-dimethoxy-phenyl)-3,4-dihydro-4-oxo-quinazoline;
6-carboxy-2-(2',5'-dimethoxy-phenyl)-3,4-dihydro-4-oxo-quinazoline;
6-carboxy-2-(2',6'-dimethoxy-phenyl)-3,4-dihydro-4-oxo-quinazoline;
6-carboxy-2-(2'-methoxy-5'-fluoro-phenyl)-3,4-dihydro-4-oxo-quinazoline.

EXAMPLE 2

4-amino-isophthalic acid (17 g) is refluxed in 800 ml of methanol and 39 ml of BF$_3$ etherate for 18 hours. After concentration under vacuum, dilute with water and filter. The precipitate is partitioned between 250 ml of ethyl acetate and 250 ml of 5% NaHCO$_3$. The aqueous phase is separated off and acidified and the precipitate filtered out and washed with water until neutral. This yields 12 g of 2-amino-5-carbomethoxybenzoic acid, which are then reacted with 60 ml of ethyl chlorocarbonate in 80 ml of dioxane under reflux for 20 hours. Add 48 ml of acetyl chloride and reflux for 72 hours. Concentrate the suspension obtained under vacuum, dilute with ethyl ether and filter. This gives 10 g of 5-carbomethoxy-isatoic anhydride (m.p. 275°–278° C.) which are treated with 25 ml of 32% ammonium hydroxide in 25 ml of dimethylformamide at room temperature for 30'. After dilution with water, the precipitate is filtered off and washed until neutral. 2-amino-5-carbomethoxybenzamide (8.1 g) is obtained, which is dissolved in 80 ml of dioxane and 10 ml of pyridine and reacted with 8 g of p-fluorobenzoylchloride at room temperature for 16 hours. After dilution with water, filter the precipitate and wash it until neutral. Crystallize from methanol, yielding 8.5 g of 2-(4'-fluorobenzoylamino)-6-carbomethoxybenzamide, which is treated with 40 ml of 2 N sodium hydroxide in 40 ml of dioxane at room temperature for 8 hours. After dilution with water and acidification, the precipitate is filtered and washed with hot ethanol to yield 7.1 g of 6-carboxy-2-(4'-fluoro-phenyl)-3,4-dihydro-4-oxo-quinazoline, m.p. 397°–399° C.

Analogously, the following compounds were obtained:

6-carboxy-2-(3'-chloro-phenyl)-3,4-dihydro-4-oxo-quinazoline, m.p. >300° C. (dec.);
6-carboxy-2-(2'-chloro-phenyl)-3,4-dihydro-4-oxo-quinazoline;
6-carboxy-2-(3'-fluoro-phenyl)-3,4-dihydro-4-oxo-quinazoline;
6-carboxy-2-(2'-fluoro-phenyl)-3,4-dihydro-4-oxo-quinazoline;
6-carboxy-2-(2'-methyl-phenyl)-3,4-dihydro-4-oxo-quinazoline;
6-carboxy-2-(3'-methyl-phenyl)-3,4-dihydro-4-oxo-quinazoline;
6-carboxy-2-(4'-methyl-phenyl)-3,4-dihydro-4-oxo-quinazoline;
6-carboxy-2-(4'-isopropyl-phenyl)-3,4-dihydro-4-oxo-quinazoline;
6-carboxy-2-(4'-tert.-butyl-phenyl)-3,4-dihydro-4-oxo-quinazoline.

EXAMPLE 3

6-carboxy-2-(2'-pyrazinyl)-4H-3,1-benzoxazin-4-one (7 g), obtained by the method of example 1, is treated with 70 ml of 32% ammonium hydroxide and refluxed for 24 hours. After cooling and acidification with acetic acid, filter and wash with ethanol, yielding 5.1 g of 6-carboxy-2-(2'-pyrazinyl)-3,4-dihydro-4-oxo-quinazoline, m.p. >300° C.

Analogously, the following compounds were obtained:

6-carboxy-2-(2'-pyridyl)-3,4-dihydro-4-oxo-quinazoline;
6-carboxy-2-(3'-methoxy-2'-pyridyl)-3,4-dihydro-4-oxo-quinazoline;
6-carboxy-2-(3'-ethoxy-2'-pyridyl)-3,4-dihydro-4-oxo-quinazoline;
6-carboxy-2-(3'-propoxy-2'-pyridyl)-3,4-dihydro-4-oxo-quinazoline;
6-carboxy-2-(3'-isopropoxy-2'-pyridyl)-3,4-dihydro-4-oxo-quinazoline;
6-carboxy-2-(3'-butoxy-2'-pyridyl)-3,4-dihydro-4-oxo-quinazoline.

EXAMPLE 4

Proceeding as described in example 2, starting from 2-amino-5-carbomethoxybenzamide and the suitable 2-alkoxy-5-amino-sulfonyl-benzoyl chlorides, the following compounds were prepared:

6-carboxy-2-(2'-methoxy-5'-aminosulfonyl-phenyl)-3,4-dihydro-4-oxo-quinazoline;
6-carboxy-2-(2'-isopropoxy-5'-aminosulfonyl-phenyl)-3,4-dihydro-4-oxo-quinazoline;
6-carboxy-2-(2'-butoxy-5'-aminosulfonyl-phenyl)-3,4-dihydro-4-oxo-quinazoline;
6-carboxy-2-(2'-methoxy-5'-N-ethylaminosulfonyl-phenyl)-3,4-dihydro-4-oxo-quinazoline;

6-carboxy-2-(2'-isopropoxy-5'-N-ethylaminosulfonyl-phenyl)-3,4-dihydro-4-oxo-quinazoline;

6-carboxy-2-(2'-butoxy-5'-N-ethylaminosulfonyl-phenyl)-3,4-dihydro-4-oxo-quinazoline;

6-carboxy-2-(2'-methoxy-5'-N-isopropylaminosulfonyl-phenyl)-3,4-dihydro-4-oxo-quinazoline;

6-carboxy-2-(2'-isopropoxy-5'-N-isopropylaminosulfonyl-phenyl)-3,4-dihydro-4-oxo-quinazoline;

6-carboxy-2-(2'-butoxy-5'-N-isopropylaminosulfonyl-phenyl)-3,4-dihydro-4-oxo-quinazoline;

6-carboxy-2-(2'-methoxy-5'-N-tert.-butylaminosulfonyl-phenyl)-3,4-dihydro-4-oxo-quinazoline;

6-carboxy-2-(2'-isopropoxy-5'-N-tert.-butylaminosulfonyl-phenyl)-3,4-dihydro-4-oxo-quinazoline;

6-carboxy-2-(2'-butoxy-5'-N-tert.-butylaminosulfonyl-phenyl)-3,4-dihydro-4-oxo-quinazoline;

6-carboxy-2-(2'-methoxy-5'-N-methyl-N-ethylaminosulfonyl-phenyl)-3,4-dihydro-4-oxo-quinazoline;

6-carboxy-2-(2'-methoxy-5'-N-methyl-N-isopropylaminosulfonylphenyl)-3,4-dihydro-4-oxo-quinazoline;

6-carboxy-2-(2'-methoxy-5'-N-methyl-N-tert.-butylaminosulfonylphenyl)-3,4-dihydro-4-oxo-quinazoline;

6-carboxy-2-(2'-methoxy-5'-N,N-diethylaminosulfonyl-phenyl)-3,4-dihydro-4-oxo-quinazoline.

EXAMPLE 5

6-carboxy-2-(2'-nitrophenyl)-3,4-dihydro-4-oxo-quinazoline (16 g), obtained by the procedure of example 1, is treated with 80 g of stannous chloride in 160 ml of glacial acetic acid and 80 ml of concentrated HCl at 50° C. for 4 hours. After cooling and diluting with water, the precipitate is filtered out and treated with 100 ml of 5% NaHCO$_3$ at 80° C. for 10'. After cooling and acidifying with acetic acid, the precipitate is filtered and washed with ethanol to yield 13.2 g of 6-carboxy-2-(2'-aminophenyl)-3,4-dihydro-4-oxo-quinazoline.

EXAMPLE 6

2-amino-5-carbomethoxybenzamide (4 g), obtained as described in example 2, is reacted with 3.4 g of 2-methoxy-benzaldehyde in the presence of 0.2 ml of piperidine in 150 ml of xylene and refluxed for 4 hours. After cooling, the precipitate is filtered out and washed with benzene. The yield is 3.3 g of 6-carbomethoxy-2-(2'-methoxyphenyl)-1,2,3,4-tetrahydro-4-oxoquinazoline, which are dissolved in 250 ml of acetone and oxidized at 0°–5° C. for 3 hours by a gradual addition of 1.8 g of finely powdered potassium permanganate. An excess of sodium bisulfite is added and after one hour the inorganic precipitate is filtered out and the acetone solution evaporated to dryness to give a residue which is crystallized from dioxane. The yield is 1.8 g of 6-carbomethoxy-2-(2'-methoxyphenyl)-3,4-dihydro-4-oxoquinazoline, which is treated with 10 ml of 1 N NaOH in 20 ml of dioxane at room temperature for 16 hours. After dilution with water and acidification, 6-carboxy-2-(2'-methoxyphenyl)-3,4-dihydro-4-oxo-quinazoline (1.4 g; m.p. 295°–297° C.), is obtained.

Analogously, the following compounds were obtained:

6-carboxy-2-(2'-isopropoxy-phenyl)-3,4-dihydro-4-oxo-quinazoline, m.p. 316°–318° C.;

6-carboxy-2-(2'-hexyloxy-phenyl)-3,4-dihydro-4-oxo-quinazoline, m.p. 198°–200° C.;

6-carboxy-2-(4'-methoxy-phenyl)-3,4-dihydro-4-oxo-quinazoline, m.p. >300° C.;

6-carboxy-2-(3'-methoxy-phenyl)-3,4-dihydro-4-oxo-quinazoline, m.p. >300° C.

EXAMPLE 7

6-carboxy-2-(2'-isopropoxyphenyl)-3,4-dihydro-4-oxo-quinazoline (7.5 g), obtained as described in example 1, is treated with an excess (2 moles/mole) of thionyl chloride in dioxane at reflux temperature for 4 hours. After cooling and concentrating to dryness under vacuum, the residue is reacted with an excess of absolute ethanol at 50° C. for 2 hours. After cooling, the precipitate is filtered and washed with ethanol and water. The yield is 6.3 g of 6-carbethoxy-2-(2'-isopropoxy-phenyl)-3,4-dihydro-4-oxo-quinazoline.

Analogously, the following compounds were obtained:

6-carbethoxy-2-(2'-methoxy-phenyl)-3,4-dihydro-4-oxo-quinazoline;

6-carbethoxy-2-[2'-(2-ethoxy-ethoxy)-phenyl]-3,4-dihydro-4-oxo-quinazoline;

6-carbethoxy-2-(2'-butoxy-phenyl)-3,4-dihydro-4-oxo-quinazoline;

6-carbethoxy-2-(2'-methoxy-5'-methyl-phenyl)-3,4-dihydro-4-oxo-quinazoline;

6-carbethoxy-2-(2'-methoxy-5'-N-isopropylaminosulfonyl-phenyl)-3,4-dihydro-4-oxo-quinazoline;

6-carbethoxy-2-(2'-methoxy-5'-N-tert.-butylaminosulfonyl-phenyl)-3,4-dihydro-4-oxo-quinazoline;

6-carbethoxy-2-(3'-methoxy-2'-pyridyl)-3,4-dihydro-4-oxo-quinazoline.

EXAMPLE 8

6-carbethoxy-2-(2'-isopropoxy-phenyl)-3,4-dihydro-4-oxo-quinazoline (5 g), obtained as described in example 7, is suspended in 100 ml of xylene and treated at reflux temperature for 4 hours with 3.9 g of phosphorus pentasulfide. After cooling, carefully add 30 ml of 10% NaOH and stir for 30' at room temperature. After neutralizing, remove the organic solvent by steam distillation. Cool and acidify to pH 4 with dilute HCl, filter and crystallize from dioxane. The yield is 2.85 g of 6-carboxy-2-(2'-isopropoxy-phenyl)-3,4-dihydro-4-thioquinazoline.

Analogously, the following compounds were obtained:

6-carboxy-2-(2'-methoxy-phenyl)-3,4-dihydro-4-thio-quinazoline;

6-carboxy-2-(2'-butoxy-phenyl)-3,4-dihydro-4-thio-quinazoline;

6-carboxy-2-(2'-methoxy-5'-methyl-phenyl)-3,4-dihydro-4-thio-quinazoline;

6-carboxy-2-(2'-methoxy-5'-N-tert.-butylaminosulfonyl-phenyl)-3,4-dihydro-4-thio-quinazoline;

6-carboxy-2-(3'-methoxy-2'-pyridyl)-3,4-dihydro-4-thio-quinazoline.

EXAMPLE 9

6-carboxy-2-[2'-(2-methyl-propoxy)-phenyl]-3,4-dihydro-4-oxo-quinazoline (23 g), obtained as described in example 1, is suspended in 200 ml of dioxane and refluxed with 12 ml of thionyl chloride for 6 hours. After cooling, the reaction mixture is treated at room temperature, with vigorous stirring and external cooling, with a slow current of dry ammonia gas for two hours. Filter the precipitate and wash till neutral with water. The yield is 22.2 g of 6-carboxamido-2-[2'-(2- methylpropoxy)-phenyl]-3,4-dihydro-4-oxo-quinazoline, which are treated with 37.5 g of p-toluenesulfonyl chloride and 33 ml of pyridine in 160 ml of dimethylformamide, at 90° C. for 5 hours. After cooling and diluting with 1.5 liters of water, filter and wash to neutral. After washing with warm isopropyl ether, the yield is 15.9 g of 6-cyano-2-[2'-(2-methylpropoxy)-phenyl]-3,4-dihydro-4-oxo-quinazoline, which are treated with 16.8 g of sodium azide and 13.8 g of ammonium chloride in 150 ml of dimethylformamide at 100° C. for 3 hours. After cooling and diluting with water, acidify to pH 4 with hydrochloric acid, filter the precipitate and wash it with water, then crystallize the product from ethanol. The yield is 11.9 g of 6-(5-tetrazolyl)-2-[2'-(2-methylpropoxy)-phenyl]-3,4-dihydro-4-oxo-quinazoline, m.p. 280° C. (dec.).

Analogously, the following compounds were obtained:
6-(5-tetrazolyl)-2-(2'-isopropoxy-phenyl)-3,4-dihydro-4-oxo-quinazoline;
6-(5-tetrazolyl)-2-(2'-methoxy-phenyl)-3,4-dihydro-4-oxo-quinazoline;
6-(5-tetrazolyl)-2-(2'-methoxy-5'-methyl-phenyl)-3,4-dihydro-4-oxo-quinazoline;
6-(5-tetrazolyl)-2-(2'-butoxy-phenyl)-3,4-dihydro-4-oxo-quinazoline;
6-(5-tetrazolyl)-2-(3'-methoxy-2'-pyridyl)-3,4-dihydro-4-oxo-quinazoline;
6-(5-tetrazolyl)-2-(3'-butoxy-2'-pyridyl)-3,4-dihydro-4-oxo-quinazoline.

EXAMPLE 10

6-carboxy-2-(2'-isopropoxy-phenyl)-3,4-dihydro-4-oxo-quinazoline (3.5 g) is treated with a hot aqueous solution of 800 mg of sodium bicarbonate. After cooling and clearing the solution by filtration, it is concentrated to a small volume and diluted with 4 volumes of acetone. Filter the precipitate and wash it with acetone. The yield is 3.2 g of the sodium salt of 6-carboxy-2-(2'-isopropoxy-phenyl)-3,4-dihydro-4-oxo-quinazoline. Analogously, the sodium salts of the following compounds were obtained:
6-carboxy-2-(2'-methoxy-phenyl)-3,4-dihydro-4-oxo-quinazoline;
6-carboxy-2-(2'-methoxy-5'-methyl-phenyl)-3,4-dihydro-4-oxo-quinazoline;
6-carboxy-2-(2'-butoxy-phenyl)-3,4-dihydro-4-oxo-quinazoline;
6-carboxy-2-(3'-methoxy-2'-pyridyl)-3,4-dihydro-4-oxo-quinazoline;
6-carboxy-2-(3'-ethoxy-2'-pyridyl)-3,4-dihydro-4-oxo-quinazoline;
6-carboxy-2-(3'-butoxy-2'-pyridyl)-3,4-dihydro-4-oxo-quinazoline.

EXAMPLE 11

6-chlorocarbonyl-2-(2'-isopropoxy-phenyl)-3,4-dihydro-4-oxo-quinazoline (7 g), prepared as described in example 7, is reacted with 2 g of 5-amino-tetrazole in 70 ml of dioxane, in the presence of 2.7 g of sodium bicarbonate, at room temperature for 6 hours. The precipitate is filtered and washed with water and then crystallized from dimethylformamide-ethanol. The yield is 4.8 g of 6-(5-tetrazolylamido)-2-(2'-isopropoxy-phenyl)-3,4-dihydro-4-oxo-quinazoline. Analogously, the following compounds were obtained:
6-(5-tetrazolylamido)-2-(2'-methoxy-phenyl)-3,4-dihydro-4-oxo-quinazoline;
6-(5-tetrazolylamido)-2-(2'-butoxy-phenyl)-3,4-dihydro-4-oxo-quinazoline;
6-(5-tetrazolylamido)-2-(2'-methoxy-5'-methyl-phenyl)-3,4-dihydro-4-oxo-quinazoline;
6-(5-tetrazolylamido)-2-(3'-methoxy-2'-pyridyl)-3,4-dihydro-4-oxo-quinazoline.

EXAMPLE 12

The sodium salt of 6-carboxy-2-(2'-isopropoxy-phenyl)-3,4-dihydro-4-oxo-quinazoline (5.6 g), prepared as described in example 10, is suspended in 50 ml of dimethylformamide and treated with 5 ml of chloromethylpivalate in the presence of 2 ml of triethylamine, at 60° C. for 16 hours. After cooling and diluting with water, extract with ethyl acetate. Wash the organic phase with 5% sodium bicarbonate and with water and then evaporate to dryness under vacuum. The residue is crystallized from ethyl ether to give the pivaloyloxymethyl ester of 6-carboxy-2-(2'-isopropoxyphenyl)-3,4-dihydro-4-oxo-quinazoline (5.2 g).

Analogously, the following compounds were obtained:
6-carboxy-2-(2'-methoxy-phenyl)-3,4-dihydro-4-oxo-quinazoline;
6-carboxy-2-(2'-ethoxy-phenyl)-3,4-dihydro-4-oxo-quinazoline;
6-carboxy-2-(2'-butoxy-phenyl)-3,4-dihydro-4-oxo-quinazoline;
6-carboxy-2-(3'-methoxy-2'-pyridyl)-3,4-dihydro-4-oxo-quinazoline.

EXAMPLE 13

Proceeding as described in example 7 and using the suitable aliphatic alcohols, the following esters of 6-carboxy-2-(2'-methoxy-phenyl)-3,4-dihydro-4-oxo-quinazoline were obtained:
isopropyl ester;
tert.-butyl ester;
octyl ester;
undecyl ester.

EXAMPLE 14

6-chlorocarbonyl-2-(2'-isopropoxy-phenyl)-3,4-dihydro-4-oxo-quinazoline (6.1 g), obtained as described in example 7, is suspended in 60 ml of dioxane and treated with 4.2 ml of diethylaminoethanol and 1 ml of triethylamine at room temperature for 18 hours. After dilution with water, the precipitate is filtered and washed to neutral, then crystallized from methanol. The yield is 5.3 g of the diethylaminoethyl ester of 6-carboxy-2-(2'-isopropoxyphenyl)-3,4-dihydro-4-oxo-quinazoline.

Analogously, the diethylamino-ethyl esters of the following compounds were obtained:
6-carboxy-2-(2'-methoxy-phenyl)-3,4-dihydro-4-oxo-quinazoline;
6-carboxy-2-(2'-ethoxy-phenyl)-3,4-dihydro-4-oxo-quinazoline;
6-carboxy-2-(2'-butoxy-phenyl)-3,4-dihydro-4-oxo-quinazoline;
6-carboxy-2-[2'-(2-ethoxy-ethoxy)-phenyl]-3,4-dihydro-4-oxo-quinazoline;
6-carboxy-2-(2'-methoxy-5'-methyl-phenyl)-3,4-dihydro-4-oxo-quinazoline;
6-carboxy-2-(3'-methoxy-2'-pyridyl)-3,4-dihydro-4-oxo-quinazoline.

EXAMPLE 15

Proceeding as described in example 14, and using as reagents either dimethylaminoethanol or N-pyrrolidylethanol or morpholinoethanol, the corresponding esters of the following compounds were obtained:
6-carboxy-2-(2'-isopropoxy-phenyl)-3,4-dihydro-4-oxo-quinazoline;
6-carboxy-2-(2'-methoxy-phenyl)-3,4-dihydro-4-oxo-quinazoline;
6-carboxy-2-(2'-butoxy-phenyl)-3,4-dihydro-4-oxo-quinazoline;
6-carboxy-2-[2'-(2-ethoxy-ethoxy)-phenyl]-3,4-dihydro-4-oxo-quinazoline;
6-carboxy-2-(2'-methoxy-5'-methyl-phenyl)-3,4-dihydro-4-oxo-quinazoline;
6-carboxy-2-(3'-methoxy-2'-pyridyl)-3,4-dihydro-4-oxo-quinazoline.

EXAMPLE 16

Dimethyl-4-amino-isophthalate (9 g) in 60 ml of dioxane and 18 ml of pyridine is treated with hexanoyl chloride (8.8 g) at room temperature for 16 hours. After dilution with water and extraction with ethyl acetate, the solution is washed with 40% citric acid and 5% NaHCO$_3$ and evaporated to dryness, so obtaining dimethyl-4-hexanoylamino-isophthalate (14.8 g) that is dissolved in 75 ml of dioxane and treated with 75 ml of 2 N NaOH at room temperature for 6 hours. After acidification with HCl the precipitate is collected under vacuum and washed until neutral. 4-hexanoylamino-isophthalic acid (11.4 g) is obtained, which is treated with 26 ml of acetic anhydride at reflux for 10'. After cooling, dilute with 30 ml of isopropyl ether and filter. 6-carboxy-2-pentyl-4H-3,1-benzoxazin-4-one (7.3 g; m.p. 185°–190° C.) is obtained, which is treated at room temperature first with 70 ml of 32% ammonium hydroxide for 16 hours and then with 50 ml of 2 N NaOH for 2 hours. After acidification with 2 N HCl, the precipitate is filtered off and crystallized from ethanol, so obtaining 6-carboxy-2-pentyl-3,4-dihydro-4-oxo-quinazoline (6.1 g; m.p. 311°–313° C.).

Analogously, the following compounds were obtained:
6-carboxy-2-propyl-3,4-dihydro-4-oxo-quinazoline;
6-carboxy-2-isopropyl-3,4-dihydro-4-oxo-quinazoline;
6-carboxy-2-(2'-methyl-propyl)-3,4-dihydro-4-oxo-quinazoline;
6-carboxy-2-(2',2'-dimethyl-propyl)-3,4-dihydro-4-oxo-quinazoline;
6-carboxy-2-hexyl-3,4-dihydro-4-oxo-quinazoline;
6-carboxy-2-heptyl-3,4-dihydro-4-oxo-quinazoline;
6-carboxy-2-nonyl-3,4-dihydro-4-oxo-quinazoline;
6-carboxy-2-undecyl-3,4-dihydro-4-oxo-quinazoline;
6-carboxy-2-(8'-cis-heptadecenyl)-3,4-dihydro-4-oxo-quinazoline;
6-carboxy-2-(2'-ethyl-pentyl)-3,4-dihydro-4-oxo-quinazoline;
6-carboxy-2-(2'-methoxy-propyl)-3,4-dihydro-4-oxo-quinazoline;
6-carboxy-2-(2'-hydroxy-propyl)-3,4-dihydro-4-oxo-quinazoline;
6-carboxy-2-butyl-3,4-dihydro-4-oxo-quinazoline;
6-carboxy-2-(1'-trans-propenyl)-3,4-dihydro-4-oxo-quinazoline;

EXAMPLE 17

Proceeding as described in example 9, the following compounds were obtained:
6-(5-tetrazolyl)-2-propyl-3,4-dihydro-4-oxo-quinazoline;
6-(5-tetrazolyl)-2-isopropyl-3,4-dihydro-4-oxo-quinazoline;
6-(5-tetrazolyl)-2-(2'-methyl-propyl)-3,4-dihydro-4-oxo-quinazoline;
6-(5-tetrazolyl)-2-(2',2'-dimethyl-propyl)-3,4-dihydro-4-oxo-quinazoline;
6-(5-tetrazolyl)-2-hexyl-3,4-dihydro-4-oxo-quinazoline;
6-(5-tetrazolyl)-2-heptyl-3,4-dihydro-4-oxo-quinazoline;
6-(5-tetrazolyl)-2-nonyl-3,4-dihydro-4-oxo-quinazoline;
6-(5-tetrazolyl)-2-undecyl-3,4-dihydro-4-oxo-quinazoline;
6-(5-tetrazolyl)-2-(8'-cis-heptadecenyl)-3,4-dihydro-4-oxo-quinazoline;
6-(5-tetrazolyl)-2-(2'-ethyl-pentyl)-3,4-dihydro-4-oxo-quinazoline;
6-(5-tetrazolyl)-2-(2'-methoxy-propyl)-3,4-dihydro-4-oxo-quinazoline;
6-(5-tetrazolyl)-2-pentyl-3,4-dihydro-4-oxo-quinazoline;
6-(5-tetrazolyl)-2-butyl-3,4-dihydro-4-oxo-quinazoline;
6-(5-tetrazolyl)-2-(1'-trans-propenyl)-3,4-dihydro-4-oxo-quinazoline.

EXAMPLE 18

Proceeding as described in example 14, the diethylaminoethyl esters and the dimethylaminoethyl esters of the compounds reported in example 17 were obtained.

EXAMPLE 19

Ethyl 4-amino-benzoate (8.5 g) dissolved in dioxane (50 ml) is reacted with hexanoyl chloride (7 g) and pyridine (7 ml) at the reflux temperature for one hour. After cooling and dilution with water, the product is extracted with ethylacetate and the organic layer is washed first with 1 N HCl and then with 5% NaHCO$_3$. Evaporation to dryness yields ethyl 4-hexanoyl-amino-benzoate (10 g) which is dissolved in dry xylene (100 ml) and reacted with ethyl carbamate (6 g) and phosphorus pentoxide (35 g) for 5 hours at the reflux temperature. After cooling, pour in ice-water, neutralize with 2 N NaOH and separate the organic layer. Evaporation to dryness yields raw 6-carbethoxy-2-pentyl-3,4-dihydro-4-oxo-quinazoline (12.1 g) which is hydrolyzed with 2 N NaOH (30 ml) in dioxane (30 ml) for 16 hours at room temperature, to give 6-carboxy-2-pentyl-3,4-dihydro-4-oxo-quinazoline (7.9 g; m.p. 310°–312° C., after crystallization from ethanol).

Analogously, the following compounds were obtained:
6-carboxy-2-butyl-3,4-dihydro-4-oxo-quinazoline;
6-carboxy-2-hexyl-3,4-dihydro-4-oxo-quinazoline;
6-carboxy-2-heptyl-3,4-dihydro-4-oxo-quinazoline.

EXAMPLE 20

Ethyl 4-(2'-methoxy-benzoylamino)-benzoate (21 g), prepared according to Example 19 is reacted with ethyl carbamate (12 g) and P$_2$O$_5$ (70 g) in xylene (200 ml) for 6 hours at the reflux temperature. After cooling, the precipitate is filtered off, poured in ice-water and treated with NaOH to neutralization. The precipitate (23 g) is collected by filtering and is hydrolyzed by treatment with LiBr (10 moles/mole) in dimethylformamide (150 ml) at the reflux temperature for 2 hours.

After cooling, acidify with acetic acid, filter and wash with hot ethanol to obtain 6-carboxy-2-(2'-methoxy-phenyl)-3,4-dihydro-4-oxo-quinazoline (14.7 g; m.p. 296°–297° C.).

Analogously, the following compounds were obtained:

6-carboxy-2-(2'-ethoxy-phenyl)-3,4-dihydro-4-oxo-quinazoline;
6-carboxy-2-(2'-isopropoxy-phenyl)-3,4-dihydro-4-oxo-quinazoline;
6-carboxy-2-(2'-butoxy-phenyl)-3,4-dihydro-4-oxo-quinazoline;
6-carboxy-2-(2'-methoxy-5'-methyl-phenyl)-3,4-dihydro-4-oxo-quinazoline;
6-carboxy-2-(2',6'-dimethoxy-phenyl)-3,4-dihydro-4-oxo-quinazoline.

We claim:

1. Compound having the following formula (I)

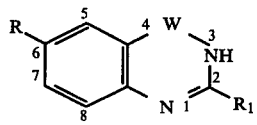

wherein
R is carboxy, the radical

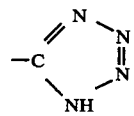

or $COOR_{11}$, wherein $R_{11}$ is $C_1$–$C_{12}$ alkyl, unsubstituted or substituted by (a) halogen, (b) carboxy, (c) $C_2$–$C_6$ carbalkoxy, (d) hydroxy, (e) $C_1$–$C_6$ alkoxy, (f) $C_2$–$C_{18}$ aliphatic acyloxy, selected from the group consisting of acetoxy, propionyloxy, stearoyloxy, pivaloyloxy and oleoyloxy (g) phenyl unsubstituted or substituted by acetyl, hydroxy, $C_1$–$C_6$ alkyl, $C_1$–$C_6$ alkoxy, halogen (h)

wherein each of $R_4$ and $R_5$ is independently hydrogen or $C_1$–$C_{10}$ alkyl or, when $R_4$ is hydrogen, $R_5$ may be (a') the radical

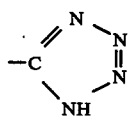

or (b') the group

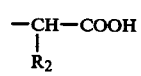

wherein $R_2$ is hydrogen or $C_1$–$C_6$ alkyl, or $R_4$ and $R_5$, taken together with the nitrogen atom, form a N-pyrrolidinyl, piperidino or morpholino radical;
$R_1$ is the radical

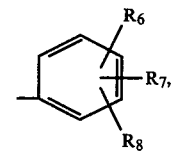

wherein each of $R_6$, $R_7$ and $R_8$, which may be the same or different, is selected from the group consisting of (a')—$(O)_m$—$R_9$ wherein m is zero or 1 and $R_9$ is $C_1$–$C_6$ alkyl, which may be unsubstituted or substituted by hydroxy or $C_1$–$C_4$ alkoxy, (b') halogen, (c')

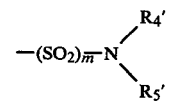

wherein each of $R'_4$ and $R'_5$, which may be the same or different, is hydrogen or $C_1$–$C_4$ alkyl, and m is defined above, and the

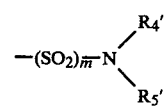

substituent is in the 2' position, and (d') hydrogen
W is $>C=O$ or $>C=S$;
and the salts thereof, either with pharmaceutically acceptable bases or with pharmaceutically acceptable acids.

2. A compound having the following formula (1)

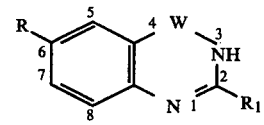

wherein
R is carboxy, the radical

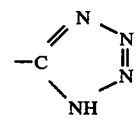

or —$COOR_{11}$, wherein
$R_{11}$ is $C_1$–$C_{12}$ alkyl, unsubstituted or substituted by $C_2$–$C_{18}$ aliphatic acyloxy, selected from the group consisting of acetoxy, propionyloxy, stearoyloxy, pivaloyloxy and oleoyloxy or by a

group, wherein
$R_4$ and $R_5$ are independently hydrogen or $C_1$–$C_{10}$ alkyl or, taken together with the nitrogen atom, form a N-pyrrolidinyl, piperidino or morpholino radical;

$R_1$ is the radical

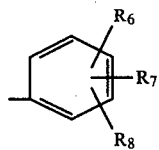

wherein each of $R_6$, $R_7$ and $R_8$, which may be the same or different, is selected from the group consisting of hydrogen; halogen; hydroxy; and —(Y)$_m$—$R_9$, wherein m is zero or 1, Y is an oxygen atom and $R_9$ is a $C_1$–$C_{12}$ alkyl or $C_3$–$C_{12}$ alkenyl, the alkyl or alkenyl group being unsubstituted or substituted by hydroxy, $C_1$–$C_6$ alkoxy, $C_2$–$C_{18}$ aliphatic acyloxy, selected from the group consisting of acetoxy, propionyloxy, stearoyloxy, pivaloyloxy and oleoyloxy;

W is >C=O;

and the salts thereof, either with pharmaceutically acceptable bases or with pharmaceutically acceptable acids.

3. A compound selected from the group consisting of:
6-carboxy-2-(2'-methoxy-phenyl)-3,4-dihydro-4-oxo-quinazoline;
6-carboxy-2-(2'-ethoxy-phenyl)-3,4-dihydro-4-oxo-quinazoline;
6-carboxy-2-(2'- allyloxy-phenyl)-3,4-dihydro-4-oxo-quinazoline;
6-carboxy-2-(2'-propoxy-phenyl)-3,4-dihydro-4-oxo-quinazoline;
6-carboxy-2-(2'-butoxy-phenyl)-3,4-dihydro-4-oxo-quinazoline;
6-carboxy-2(2'-isopropoxy-phenyl)-3,4-dihydro-4-oxo-quinazoline;
6-carboxy-2-[2'-(1-methyl-propoxy)-phenyl]-3,4-dihydro-4-oxo-quinazoline;
6-carboxy-2-[2'-(2-methyl-propoxy)-phenyl]-3,4-dihydro-4-oxo-quinazoline;
6-carboxy-2-[2'-(2-ethoxy-ethoxy)-phenyl]-3,4-dihydro-4-oxo-quinazoline;
6-carboxy-2-[4'-(2-ethoxy-ethoxy)-phenyl]-3,4-dihydro-4-oxo-quinazoline;
6-carboxy-2-(2'-fluoro-phenyl)-3,4-dihydro-4-oxo-quinazoline;
6-carboxy-2-(3'-fluoro-phenyl)-3,4-dihydro-4-oxo-quinazoline;
6-carboxy-2-(4'-fluoro-phenyl)-3,4-dihydro-4-oxo-quinazoline;
6-carboxy-2-(2'-chloro-phenyl)-3,4-dihydro-4-oxo-quinazoline;
6-carboxy-2-(2'-methyl-phenyl)-3,4-dihydro-4-oxo-quinazoline;
6-carboxy-2-(3'-methyl-phenyl)-3,4-dihydro-4-oxo-quinazoline;
6-carboxy-2-(4'-methyl-phenyl)-3,4-dihydro-4-oxo-quinazoline;
6-carboxy-2-(4'-isopropyl-phenyl)-3,4-dihydro-4-oxo-quinazoline;
6-carboxy-2-(3',4'-dimethoxy-phenyl)-3,4-dihydro-4-oxo-quinazoline;
6-carboxy-2-(2'-amino-phenyl)-3,4-dihydro-4-oxo-quinazoline;
6-carboxy-2-(2'-methoxy-5'-methyl-phenyl)-3,4-dihydro-4-oxo-quinazoline;
6-carboxy-2-(2'-methoxy-4'-methyl-phenyl)-3,4-dihydro-4-oxo-quinazoline;
6-carboxy-2-(2'-isopropoxy-5'-methyl-phenyl)-3,4-dihydro-4-oxo-quinazoline;
6-carboxy-2-(2'-isopropoxy-4'-methyl-phenyl)-3,4-dihydro-4-oxo-quinazoline;
6-carboxy-2-(2'-butoxy-5'-methyl-phenyl)-3,4-dihydro-4-oxo-quinazoline;
6-carboxy-2-(2'-butoxy-4'-methyl-phenyl)-3,4-dihydro-4-oxo-quinazoline;
6-carboxy-2-(2',5'-dimethoxy-phenyl)-3,4-dihydro-4-oxo-quinazoline;
6-carboxy-2-(2',6'-dimethoxy-phenyl)-3,4-dihydro-4-oxo-quinazoline;
6-carboxy-2-(2',4'-dimethoxy-phenyl)-3,4-dihydro-4-oxo-quinazoline;
6-carboxy-2-(2'-methoxy-5'-fluoro-phenyl)-3,4-dihydro-4-oxo-quinazoline;
6-carboxy-2-(2'-methoxy-5'-aminosulfonyl-phenyl)-3,4-dihydro-4-oxo-quinazoline;
6-carboxy-2-(2'-isopropoxy-5'-aminosulfonyl-phenyl)-3,4-dihydro-4-oxo-quinazoline;
6-carboxy-2-(2'-butoxy-5'-aminosulfonyl-phenyl)-3,4-dihydro-4-oxo-quinazoline;
6-carboxy-2-(2'-methoxy-5'-N-ethylaminosulfonyl-phenyl)-3,4-dihydro-4-oxo-quinazoline;
6-carboxy-2-(2'-isopropoxy-5'-N-ethylaminosulfonyl-phenyl)-3,4-dihydro-4-oxo-quinazoline;
6-carboxy-2-(2'-butoxy-5'-N-ethylaminosulfonyl-phenyl)-3,4-dihydro-4-oxo-quinazoline;
6-carboxy-2-(2'-methoxy-5'-N-isopropylaminosulfonyl-phenyl)-3,4-dihydro-4-oxo-quinazoline;
6-carboxy-2-(2'-isopropoxy-5'-N-isopropylaminosulfonyl-phenyl)-3,4-dihydro-4-oxo-quinazoline;
6-carboxy-2-(2'-butoxy-5'-N-isopropylaminosulfonyl-phenyl)-3,4-dihydro-4-oxo-quinazoline;
6-carboxy-2-(2'-methoxy-5'-N-tertbutylaminosulfonyl-phenyl)-3,4-dihydro-4-oxo-quinazoline;
6-carboxy-2-(2'-isopropoxy-5'-N-tertbutylaminosulfonyl-phenyl)-3,4-dihydro-4-oxo-quinazoline;
6-carboxy-2-(2'-butoxy-5'-N-tertbutylaminosulfonyl-phenyl)-3,4-dihydro-4-oxo-quinazoline;
6-carboxy-2-(2'-methoxy-5'-N-methyl-N-ethylaminosulfonyl-phenyl)-3,4-dihydro-4-oxo-quinazoline;
6-carboxy-2-(2'-methoxy-5'-N-methyl-N-isopropylaminosulfonyl-phenyl)-3,4-dihydro-4-oxo-quinazoline;
6-carboxy-2-(2'-methoxy-5'-N-methyl-N-tertbutylaminosulfonyl-phenyl)-3,4-dihydro-4-oxo-quinazoline;
6-carboxy-2-(2'-methoxy-5'-N,N-diethylaminosulfonyl-phenyl)-3,4-dihydro-4oxo-quinazoline;
6-(5-tetrazolyl)-2-(2'-ethoxy-phenyl)-3,4-dihydro-4-oxo-quinazoline;
6-(5-tetrazolyl)-2-(2'-methoxy-phenyl)-3,4-dihydro-4-oxo-quinazoline;
6-(5-tetrazolyl)-2-(2'-butoxy-phenyl)-3,4-dihydro-4-oxo-quinazoline;
6-(5-tetrazolyl)-2-(2'-isopropoxy-phenyl)-3,4-dihydro-4-oxo-quinazoline;
6-(5-tetrazolyl)-2-(2'-methoxy-4'-methyl-phenyl)-3,4-dihydro-4-oxo-quinazoline;
6-(5-tetrazolyl)-2-(2'-methoxy-5'-methyl-phenyl)-3,4-dihydro-4-oxo-quinazoline;
6-(5-tetrazolyl)-2-(2',6'-dimethoxy-phenyl)-3,4-dihydro-4-oxo-quinazoline;

6-carboxy-2-(2'-iropropoxy-phenyl)-3,4-dihydro-4-thio-quinazoline;

6-carboxy-2-(2'-butoxy-phenyl)-3,4-dihydro-4-thio-quinazoline;

6-carboxy-2-(2'-methoxy-phenyl)-3,4-dihydro-4-thio-quinazoline, and the pharmaceutically acceptable salts thereof.

4. A compound selected from the group consisting of:
6-carboxy-2-(2'-methoxy-phenyl)-3,4-dihydro-4-oxo-quinazoline;
6-carboxy-2-(2'-ethoxy-phenyl)-3,4-dihydro-4-oxo-quinazoline;
6-carboxy-2-(2'-allyloxy-phenyl)-3,4-dihydro-4-oxo-quinazoline;
6-carboxy-2-(2'-propoxy-phenyl)-3,4-dihydro-4-oxo-quinazoline;
6-carboxy-2-(2'-butoxy-phenyl)-3,4-dihydro-4-oxo-quinazoline;
6-carboxy-2(2'-isopropoxy-phenyl)-3,4-dihydro-4-oxo-quinazoline;
6-carboxy-2-[2'-(1-methyl-propoxy)-phenyl]-3,4-dihydro-4-oxo-quinazoline;
6-carboxy-2-[2'-(2-methyl-propoxy)-phenyl]-3,4-dihydro-4-oxo-quinazoline;
6-carboxy-2-[2'-(2-ethoxy-ethoxy)-phenyl]-3,4-dihydro-4-oxo-quinazoline;
6-carboxy-2[4'-(2-ethoxy-ethoxy)-phenyl]-3,4-dihydro-4-oxo-quinazoline;
6-carboxy-2-(2'-fluoro-phenyl)-3,4-dihydro-4-oxo-quinazoline;
6-carboxy-2-(3'-fluoro-phenyl)-3,4-dihydro-4-oxo-quinazoline;
6-carboxy-2-(4'-fluoro-phenyl)-3,4-dihydro-4-oxo-quinazoline;
6-carboxy-2-(2'-chloro-phenyl)-3,4-dihydro-4-oxo-quinazoline;
6-carboxy-2-(2'-methyl-phenyl)-3,4-dihydro-4-oxo-quinazoline;
6-carboxy-2-(3'-methyl-phenyl)-3,4-dihydro-4-oxo-quinazoline;
6-carboxy-2-(4'-methyl-phenyl)-3,4-dihydro-4-oxo-quinazoline;
6-carboxy-2-(4'-isopropyl-phenyl)-3,4-dihydro-4-oxo-quinazoline;
6-carboxy-2-(3',4'-dimethoxy-phenyl)-3,4-dihydro-4-oxo-quinazoline;
6-carboxy-2-(2'-methoxy-5'-methyl-phenyl)-3,4-dihydro-4-oxo-quinazoline;
6-carboxy-2-(2'-methoxy-4'-methyl-phenyl)-3,4-dihydro-4-oxo-quinazoline;
6-carboxy-2-(2'-isopropoxy-5'-methyl-phenyl)-3,4-dihydro-4-oxo-quinazoline;
6-carboxy-2-(2'-isopropoxy-4'-methyl-phenyl)-3,4-dihydro-4-oxo-quinazoline;
6-carboxy-2-(2'-butoxy-5'-methyl-phenyl)-3,4-dihydro-4-oxo-quinazoline;
6-carboxy-2-(2'-butoxy-4'-methyl-phenyl)-3,4-dihydro-4-oxo-quinazoline;
6-carboxy-2-(2',5'-dimethoxy-phenyl)-3,4-dihydro-4-oxo-quinazoline;
6-carboxy-2-(2',6'-dimethoxy-phenyl)-3,4-dihydro-4-oxo-quinazoline;
6-carboxy-2-(2',4'-dimethoxy-phenyl)-3,4-dihydro-4-oxo-quinazoline;
6-carboxy-2-(2'-methoxy-5'-fluoro-phenyl)-3,4-dihydro-4-oxo-quinazoline;
and pharmaceutically acceptable salts thereof.

5. A pharmaceutically acceptable salt of the compound of claim 4, wherein said salt is the sodium salt.

6. A compound selected from the group consisting of:
the diethylamino-ethyl ester of the compound 6-carboxy-2-(2'-ethoxy-phenyl)-3,4-dihydro-4-oxo-quinazoline;
the diethylamino-ethyl ester of the compound 6-carboxy-2-(2'-methoxy-5'-methyl-phenyl)-3,4-dihydro-4-oxo-quinazoline;
and the pharmaceutically acceptable salts thereof.

7. A pharmaceutically acceptable salt of the compound of claim 6 wherein said salt is the hydrochloride salt.

8. A compound selected from the group consisting of:
6-(5-tetrazolyl)-2-(2'-ethoxy-phenyl)-3,4-dihydro-4-oxo-quinazoline;
6-(5-tetrazolyl)-2-(2'-methoxy-phenyl)-3,4-dihydro-4-oxo-quinazoline;
6-(5-tetrazolyl)-2-(2'-butoxy-phenyl)-3,4-dihydro-4-oxo-quinazoline;
6-(5-tetrazolyl)-2-(2'-isopropoxy-phenyl)-3,4-dihydro-4-oxo-quinazoline;
6-(5-tetrazolyl)-2-(2'-methoxy-4'-methyl-phenyl)-3,4-dihydro-4-oxo-quinazoline;
6-(5-tetrazolyl)-2-(2'-methoxy-5'-methyl-phenyl)-3,4-dihydro-4-oxo-quinazoline;
6-(5-tetrazolyl)-2-(2',6'-dimethoxy-phenyl)-3,4-dihydro-4-oxo-quinazoline.

9. An ester of a compound selected from the group consisting of:
6-carboxy-2-(2'-methoxy-phenyl)-3,4-dihydro-4-oxo-quinazoline;
6-carboxy-2-(2'-ethoxy-phenyl)-3,4-dihydro-4-oxo-quinazoline;
6-carboxy-2-(2'-allyloxy-phenyl)-3,4-dihydro-4-oxo-quinazoline;
6-carboxy-2-(2'-propoxy-phenyl)-3,4-dihydro-4-oxo-quinazoline;
6-carboxy-2-(2'-butoxy-phenyl)-3,4-dihydro-4-oxo-quinazoline;
6-carboxy-2(2'-isopropoxy-phenyl)-3,4-dihydro-4-oxo-quinazoline;
6-carboxy-2-[2'-(1-methyl-propoxy)-phenyl]-3,4-dihydro-4-oxo-quinazoline;
6-carboxy-2-[2'-(2-methyl-propoxy]-3,4-dihydro-4-oxo-quinazoline;
6-carboxy-2-[2'-(2-ethoxy-ethoxy)-phenyl]-3,4-dihydro-4-oxo-quinazoline;
6-carboxy-2-[4'-(2-ethoxy-ethoxy)-phenyl]-3,4-dihydro-4-oxo-quinazoline;
6-carboxy-2-(2'-fluoro-phenyl)-3,4-dihydro-4-oxo-quinazoline;
6-carboxy-2-(3'-fluoro-phenyl)-3,4-dihydro-4-oxo-quinazoline;
6-carboxy-2-(4'-fluoro-phenyl)-3,4-dihydro-4-oxo-quinazoline;
6-carboxy-2-(2'-chloro-phenyl)-3,4-dihydro-4-oxo-quinazoline;
6-carboxy-2-(2'-methyl-phenyl)-3,4-dihydro-4-oxo-quinazoline;
6-carboxy-2-(3'-methyl-phenyl)-3,4-dihydro-4-oxo-quinazoline;
6-carboxy-2-(4'-methyl-phenyl)-3,4-dihydro-4-oxo-quinazoline;
6-carboxy-2-(4'-isopropyl-phenyl)-3,4-dihydro-4-oxo-quinazoline;
6-carboxy-2-(3',4'-dimethoxy-phenyl)-3,4-dihydro-4-oxo-quinazoline;

6-carboxy-2-(2'-methoxy-5'-methyl-phenyl)-3,4-dihydro-4-oxo-quinazoline;

6-carboxy-2-(2'-methoxy-4'-methyl-phenyl)-3,4-dihydro-4-oxo-quinazoline;

6-carboxy-2-(2'-isopropoxy-5'-methyl-phenyl)-3,4-dihydro-4-oxo-quinazoline;

6-carboxy-2-(2'-isopropoxy-4'-methyl-phenyl)-3,4-dihydro-4-oxo-quinazoline;

6-carboxy-2-(2'-butoxy-5'-methyl-phenyl)-3,4-dihydro-4-oxo-quinazoline;

6-carboxy-2-(2'-butoxy-4'-methyl-phenyl)-3,4-dihydro-4-oxo-quinazoline;

6-carboxy-2-(2',5'-dimethoxy-phenyl)-3,4-dihydro-4-oxo-quinazoline;

6-carboxy-2-(2',6'-dimethoxy-phenyl)-3,4-dihydro-4-oxo-quinazoline;

6-carboxy-2-(2',4'-dimethoxy-phenyl)-3,4-dihydro-4-oxo-quinazoline;

6-carboxy-2-(2'-methoxy-5'-fluoro-phenyl)-3,4-dihydro-4-oxo-quinazoline;

wherein said ester is an alkyl ester or a pivaloyloxymethyl ester, and wherein the alkyl group is selected from the group consisting of ethyl, isopropyl, t-butyl, and octyl.

10. An antiallergic pharmaceutical composition comprising a compound of claim 1 and a pharmaceutically acceptable carrier and/or diluent therefor.

11. Method of treating an allergy selected from the group consisting of bronchial asthma, allergic rhinitis, hay fever, urticaria or dermatosis, said method comprising administring to a host having said allergy a therapeutically affective amount of a compound of claim 1.

12. Method of claim 11, wherein the compound is administered orally.

13. Method of claim 11, wherein the compound is administered by inhalation.

14. Method of claim 11, wherein the compound is administered by topical application.

15. Method of claim 11, wherein the compound is administered parenterally.

* * * * *